United States Patent [19]

Hardy

[11] Patent Number: 4,840,622
[45] Date of Patent: Jun. 20, 1989

[54] KINK RESISTANT CATHETER

[75] Inventor: Dwayne E. Hardy, San Mateo, Calif.

[73] Assignee: Menlo Care, Inc., Palo Alto, Calif.

[21] Appl. No.: 105,552

[22] Filed: Oct. 6, 1987

[51] Int. Cl.⁴ .............................................. A61M 5/00
[52] U.S. Cl. ................................... 604/264; 604/280;
128/348.1
[58] Field of Search ................ 604/280, 282, 164–170,
604/264, 265, 93; 128/268, 348.1

[56] References Cited

U.S. PATENT DOCUMENTS

| 4,046,144 | 9/1977 | McFarlane | 604/168 |
| 4,434,797 | 3/1984 | Silander | 604/264 |
| 4,596,563 | 6/1986 | Pande | 604/280 X |
| 4,610,671 | 9/1986 | Luther | 604/264 X |

OTHER PUBLICATIONS

Centrasil with J wire; Silicone Elastomer Central Venous Cathether with J14 wire, Baxter Travenol Labs, Inc. 9/84.

*Primary Examiner*—Stephen C. Pellegrino
*Attorney, Agent, or Firm*—Fliesler, Dubb, Meyer & Lovejoy

[57] ABSTRACT

An improvement is set forth in a cannula having a proximal end portion adapted to be connected to a hub, a distal end portion and a longitudinal duct therethrough from the distal end portion to the proximal end portion. The improvement is wherein the cannula has a larger outer cross-section and the duct has a larger inner cross-section starting from the proximal end portion and continuing to a position along the cannula then have the cannula and duct starting at the distal end portion and continuing to the position. The position is located distally from the hub. A reinforcing tube is provided having an outer surface matingly held within the duct and an inner passageway, the tube extending from the proximal end portion distally beyond the hub towards the position. That portion of the cannula which is reinforced by the reinforcing tube is prevented from kinking and/or deforming.

46 Claims, 4 Drawing Sheets

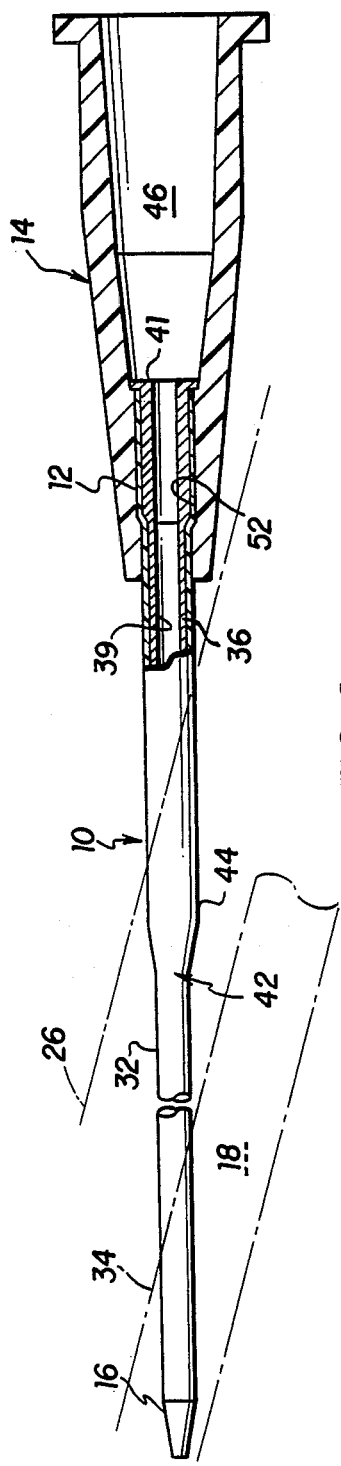
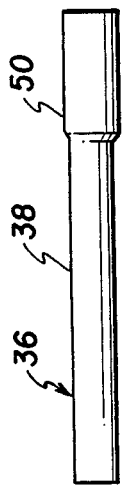
FIG. 1
FIG. 2

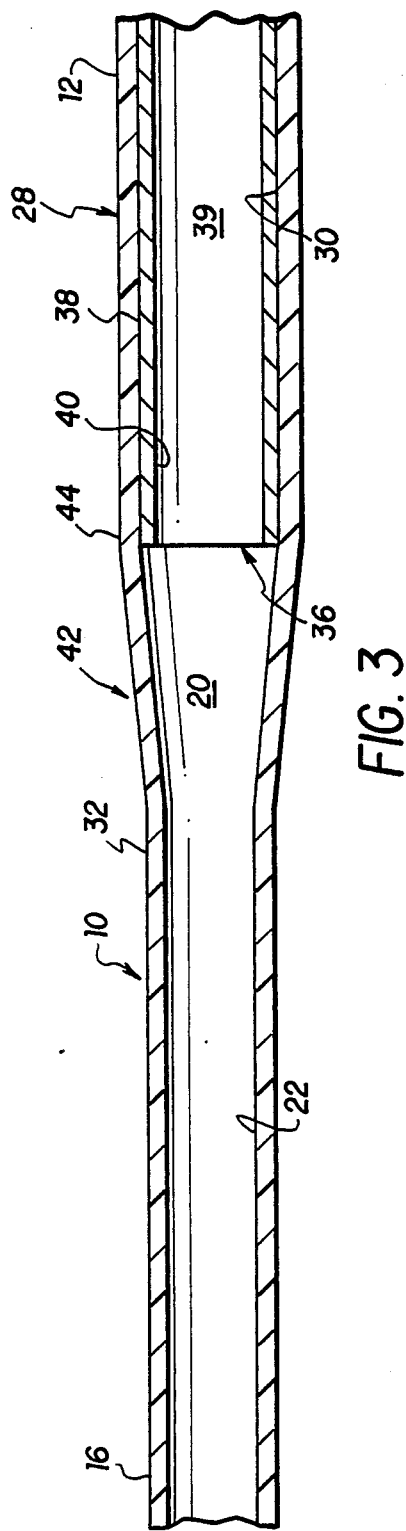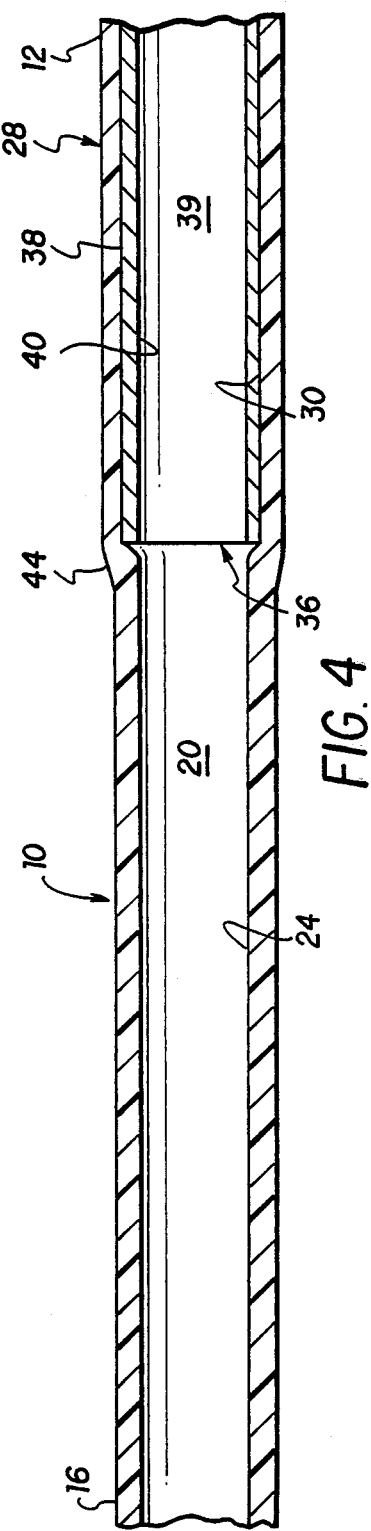

KINK RESISTANT CATHETER

FIELD OF THE INVENTION

The invention relates to a cannula of the over-the-needle type for insertion into a blood vessel of a patient.

BACKGROUND OF THE INVENTION

A number of catheter assemblies are known for introduction of a polymeric cannula into a vein, artery or cavity of a living subject for infusion or extraction of fluids. A widely used method of inserting such a polymeric cannula is to position a steel needle (or solid stylet) within the duct of a cannula with the tip of the needle or stylet extending from the distal end of the cannula. The needle or stylet is then inserted into a living subject after which the needle or stylet is removed from the cannula, leaving the cannula behind with at least its distal end in the subject. Additional tubing can be attached to the cannula or medicaments or nutrients can be caused to flow through the cannula into the subject.

The cannulae of the prior art have generally been made of a rigid material which does not soften and/or exhibit a change in the cross-sectional area of the duct of the cannula after insertion into a vein. More recently, as set forth in commonly assigned co-pending U.S. Application Ser. No. 780,543, filed Sept. 26, 1985, now abandoned materials have been developed which can be formulated into cannulae and which, while they are rigid enough to retain their shape during insertion, also have the property of both softening and swelling to form an enlarged duct cross-section on insertion in a blood vessel due to water pickup. Also, recent publications discuss cannulae which soften on being raised to a temperature approaching body temperature.

The cannulae which form enlarged ducts can soften on formation of such enlarged ducts. This has introduced a problem in that the softened portion of the cannulae which extends outwardly from the skin of the patient can kink or be deformed, thereby cutting off flow of nutrients, medicaments and the like, into the vein. A kinking problem also exists to an extent with the prior art rigid cannulae which are generally quite thin. To date, the art has not provided an adequate solution to these problems.

The present invention is directed to overcoming one or more of the problems as set forth above.

DISCLOSURE OF THE INVENTION

In accordance with an aspect of the present invention an improvement is set forth in a cannula having a proximal end portion adapted to be connected to a hub, a distal end portion and a longitudinal duct there through from the distal end portion to the proximal end portion. The improvement comprises wherein the cannula has a larger outer cross-section and the duct has a larger inner cross-section starting from the proximal end portion and continuing to a position along the cannula than have the cannula and the duct starting at the distal end portion and continuing to the position. The position is located distally from the hub. A reinforcing tube having an outer surface is matingly held within the duct, the reinforcing tube having an inner passageway. The tube extends from the proximal end portion distally beyond the hub towards the position.

In accordance with another aspect of the present invention an improvement is set forth in a cannula having a proximal end portion adapted to be connected to a hub, a distal end portion and a longitudinal duct therethrough from the distal end portion to the proximal end portion. The improvement comprises wherein the cannula has a larger outer cross-section and the duct has a larger inner cross-section starting from the proximal end portion and continuing to a position along the cannula than have the cannula and the duct starting at the distal end portion and continuing to the position. The position is located such that when the distal end portion is inserted in the blood vessel the position is located beneath the skin but short of the blood vessel. A reinforcing tube having an outer surface is matingly held within the duct, the reinforcing tube having an inner passageway. The tube extends from the proximal end portion to adjacent the position.

In accordance with yet another aspect of the present invention an improvement is set forth in a cannula having a proximal end portion adapted to be connected to a hub, a distal end portion and a longitudinal duct therethrough from the distal end portion to the proximal end portion, the cannula being of a material selected such that an inner cross-section of the duct increases to form an enlarged duct cross-section when at least a part of the distal end portion is inserted through the skin and into a blood vessel of a living subject and maintained therein and/or when the duct is contacted by an aqueous liquid for a period of time sufficient for the enlarged duct cross-section to form. The improvement comprises wherein the cannula has a larger outer cross-section and the duct has a larger inner cross-section starting from the proximal end portion and continuing to a position along the cannula than have the cannula and the duct starting at the distal end portion and continuing to the position. The position is located such that when the distal end portion is inserted in the blood vessel the position is located beneath the skin but short of the blood vessel. A reinforcing tube having an outer surface is matingly held within the duct, the reinforcing tube having an inner passageway. The tube extends from the proximal end portion to adjacent the position.

The reinforcing tube greatly reduces the possibility of kinking of at least a portion of the cannula section which extends from the patients skin to the hub. Thus the kinking problem is alleviated. One can, if desired, reap the benefits of utilizing a cannula material which softens whereby irritation of the vein wall is minimized and/or which enlarges, thereby also serving to minimize irritation of the vein wall (since the puncturing needle or stylet can be relatively small for a desired duct size).

BRIEF DESCRIPTION OF THE DRAWING

The invention will be better understood by reference to the figures of the drawings, wherein:

FIG. 1 illustrates, in side partially sectioned view, a cannula structure in accordance with an embodiment of the present invention attached to a hub;

FIG. 2 illustrates, in side view, a reinforcing tube useful with the embodiment of FIG. 1;

FIG. 3 illustrates, in partial enlarged view in side section, the cannula structure of FIG. 1 with the cannula not enlarged;

FIG. 4 is a view like FIG. 3 but with the cannula enlarged;

BEST MODE FOR CARRYING OUT THE INVENTION

Figure 5:
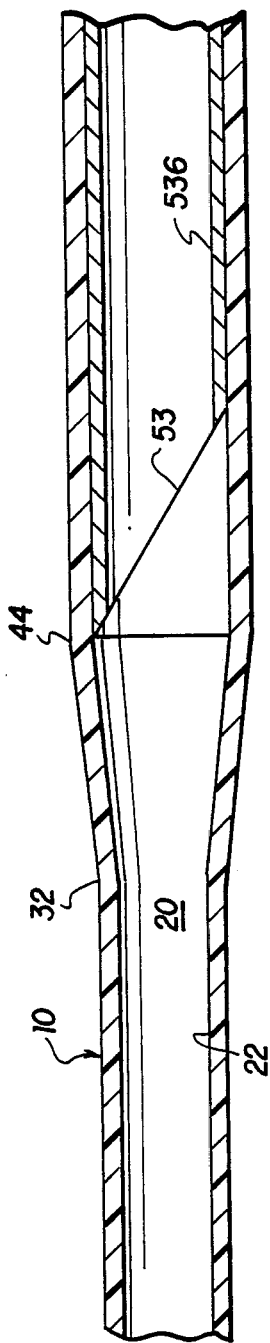
FIG. 5 is a view like FIG. 3 but of an alternative reinforcing tube.

Referring to FIGS. 1, 3 and 4, a cannula 10 in accordance with the present invention is illustrated. The cannula 10 has a proximal end portion 12 adapted to be connected to a hub 14. A distal end portion 16 of the cannula 10 is adapted for inserting in a blood vessel 18 of a living subject. A longitudinal duct 20 (see FIGS. 3 and extends through the cannula 10 from the distal end portion 16 to the proximal end portion 12.

The cannula 10 can be formulated of a material selected such that it softens in the area having an inner cross-section 22 (FIG. 3) when at least a part of the distal portion 16 of the cannula 10 is inserted through the skin 26 and into the blood vessel 18 of a living subject and is maintained therein and/or when the duct 20 is contacted by an aqueous liquid for a period of time sufficient for the enlarged duct cross-section 24 to form. The material can be such that an inner cross-section 22 (FIG. 3) of the duct 20 increases to form an enlarged duct cross-section 24 (FIG. 4) under such circumstances. Alternatively, the cannula can be formulated of a non-softening and/or non-swelling material such as Teflon (trademark of Dupont).

The cannula 10 of the present invention is unique in that it has a larger outer cross-section at 28 and said duct 20 has a larger inner cross-section at 30 starting from the proximal end portion 12 and continuing to a position 32 along the cannula than have the cannula 10 and duct 20 starting at the distal end portion 16 and continuing to the position 32. In accordance with certain aspects of the present invention it is desirable that the position 32 be located such that when the distal end portion 16 is inserted in the blood vessel 18, the position 32 is then located beneath the skin 26 but short of the proximal wall 34 of the blood vessel 18.

Further in accordance with the present invention (see FIG. 2) a reinforcing tube 36, having an outer surface 38 and an inner passageway 39, is matingly held within the duct 20 and over a metal insert 41 and extends from the proximal end portion 12 of the cannula 10 and beyond the hub 14. In this manner the reinforcing tube 36 reinforces at least a portion of that section of the cannula 10 extending distally beyond the hub 14. In accordance with certain aspects of the invention the reinforcing tube 36 extends to adjacent the position 32 along the cannula 10. When this is the case, and when the position 32 is located such that it is beneath the skin 26 when the distal end portion 16 is inserted in the blood vessel 18, the reinforcing tube 36 is aligned, after insertion of the distal end portion 16 of the cannula 10 in the blood vessel 18, through the skin 26 and serves to reinforce that portion of the cannula 10 which extends to the hub 14. This serves to prevent kinking and/or deformation of the cannula 10 outside of the patient's body along its entire length up to the hub 14.

The inner passageway 39 of the reinforcing tube 36 has an inside cross-section 40 which can suitably be substantially equal to or greater than the enlarged duct cross-section 24 at the distal end portion 16 of the cannula 10 when the cannula is of a material which forms such an enlarged duct cross-section 24 (as in FIG. 4). When the cannula 10 is not of a material which forms an enlarged duct cross-section 24, the inner passageway 39 of the reinforcing tube 36 should have its inside cross-section 40 substantially equal to or greater than the (unchanging) inner cross-section 22. The reinforcing tube 36 is suitably made of a polymeric material, most suitably of a plastic material. Suitable materials include, e.g., polyurethane, polyvinylchloride and polyethylene. However, the material of the reinforcing tube 36 is not critical. Accordingly, other materials can also be used. Of course, the material chosen should not be such as to introduce contaminants or interfere with analysis should the cannula 10 be used for sampling.

The material of the reinforcing tube 36 preferably exhibits a 2.5% Secant modulus between about 3450 Newtons/square centimeter (N/cm$^2$) to about 48,000 N/cm$^2$, more preferably from about 6900 N/cm$^2$ to about 34,500 N/cm$^2$.

The cannula 10 generally includes a tapered section 42 which extends from the position 32 towards the proximal end portion 12 of the cannula 10 to an end of taper location 44. The end of taper location 44 is adjacent the position 32. The taper can be conical, as illustrated, or can be a smooth curving taper. The reinforcing tube 36 of FIG. 2 terminates at the end of taper location 44. Suitably the tapered section 42 is tapered at an angle of less than 45° (from the longitudinal extension of the cannula 10), preferably no more than about 15° and still more preferably no more than about 5°. This helps to ensure that the cannula 10 advances smoothly through the skin 26.

The reinforcing tube 36 can also serve to attach or hold the proximal end portion 12 of the cannula 10 in a bore 46 of the hub 14. As illustrated in FIG. 1, the proximal end portion 12 of the cannula 10 and the reinforcing tube 36 can be forced over the metal insert 41 and then press fit into the mating cavity 52 of the hub 14.

Suitably the material of the cannula 10 is selected whereby the tapered section 42 is strong enough so that it does not crinkle or give sufficiently to cause problems when the distal end portion 16 of the cannula 10 is inserted into the blood vessel 18.

FIG. 5 shows an alternative reinforcing tube 536 which extends to adjacent the position 32, specifically to the end of taper location 44, but which is cut away along 53 to ease the transition from the unreinforced cannula 10 distal of the reinforcing tube 536 to the proximal end portion 12 of the cannula 10 as reinforced by the reinforcing tube 536.

Figure 6:
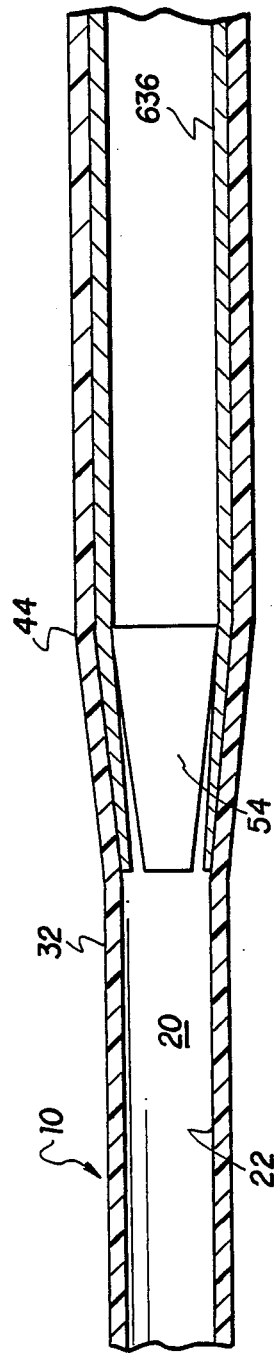
FIG. 6 is a view like FIG. 3 but of another alternative reinforcing tube.

FIG. 6 shows another alternative reinforcing tube 636 having one or more fingers 54 which extend to the position 32. The fingers 54 and the reinforcing tube 636 are formulated of a material having elastic properties and, in the case where the cannula 10 forms an enlarged duct cross-section 24, the fingers 54 are suitably self-impelled to straighten out so as not to impede fluid flow through the longitudinal duct 20. The embodiment of FIG. 6, like that of FIG. 5, thus includes means for easing the transition from the unreinforced cannula 10 distal of the reinforcing tube 536 or 636 to the reinforced cannula 10 proximal the reinforcing tube 536 or 636. Although not illustrated the alternative reinforcing tubes 536, 636 can extend to between the position 32 and the end of taper location 44.

Figure 7:
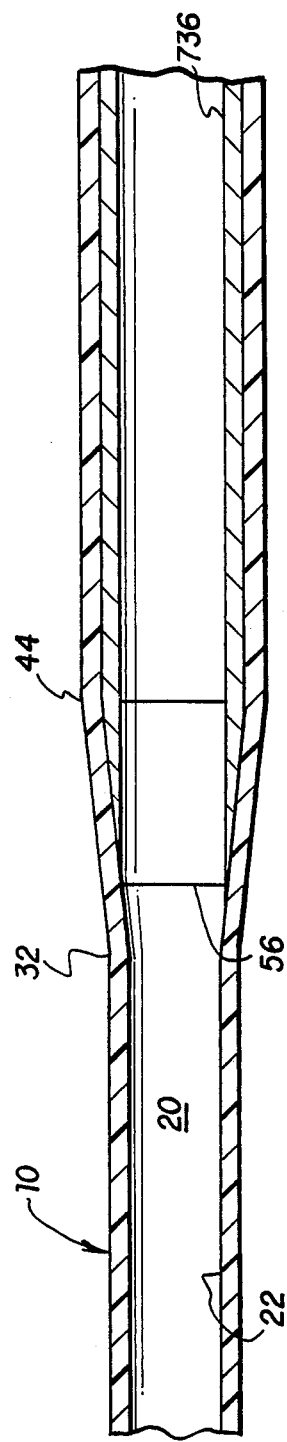
FIG. 7 is a view like FIG. 3 but of still another alternative reinforcing tube.

FIG. 7 shows still another alternative reinforcing tube 736 which tapers or thins towards its distal end 56 which extends to adjacent the position 32 and between the position 32 and the end of the taper location 44. The thinned distal end 56 thus serves as alternative means for easing transition from the unreinforced cannula 10 distal of the reinforcing tube 736 to the reinforced cannula 10 proximal the reinforcing tube 736.

As has been pointed out above the present invention is useful with any cannula 10 including when the cannula 10 is formulated of a material that softens on insertion into the body. The invention is particularly useful with such softening cannulae 10 when the material is such that the inner cross-section 22 of the duct 20 increases to form the enlarged duct cross-sectional area 24, generally enlarged from at least about 25% (to 125% of its initial inner cross-section) to at least about 300%, more preferably from about 40% to about 300% ; still more preferably from about 35% to about 140% , and most preferably from about 40% to about 100%, when at least a part of the distal end portion 16 of the cannula 10 is inserted in to a body, generally into the blood vessel 18, of a living subject and maintained in contact with that body and/or when the duct 20 is contacted by, e.g., filled with, an aqueous liquid, for a time sufficient for the enlarged duct cross-section 24 to form.

In accordance with one embodiment of the present invention the cannula comprises a multiple phase polymeric composition comprising a first phase which comprises a substantially non-hydrophilic polymeric component and a second phase which comprises a hydrophilic polymeric component. The relative amounts of these components are selected, depending on the particular polymeric materials employed, to provide a composition having the desired properties, as discussed more fully below.

Preferably the non-hydrophilic polymeric component forms a continuous phase. The hydrophilic polymeric component can form a co-continuous phase with, or a dispersed phase in, the non-hydrophilic polymer phase.

The non-hydrophilic polymeric component comprises a polymer which does not substantially absorb or attract water. Preferably, the non-hydrophilic polymer is capable of absorbing an amount of no more than about 30% water, more preferably no more than about 15%, and most preferably no more than about 10%, by weight, based on the weight of the non-hydrophilic polymer.

The non-hydrophilic polymer can be for example, a polyurethane such as an aliphatic polyurethane, a polyether polyurethane, a polyester polyurethane; an ethylene copolymer such as ethylene-vinyl acetate copolymer; a polyamide, in particular a polyamide of low crystallinity; an aliphatic polyester; or the like. A particularly preferred non-hydrophilic polymer is a polyurethane, especially an aliphatic polyurethane.

The hydrophillic polymer preferably is a polymer that absorbs at least about 50% water, more preferably about 100%, for example, at least about 150%, by weight based on the weight of the hydrophilic polymer. The hydrophilic polymer preferably forms a hydrogel on absorption of water.

The hydrophilic polymer is preferably polyvinyl alcohol, poly(ethylene oxide), polypropylene oxide, poly (ethylene glycol), polypropylene glycol, polytetramethylene oxide, polyvinyl pyrolidene, polyacrylamide, poly (hydroxyethyl acrylate), poly (hydroxyethyl methacrylate), or the like.

The multiple phase composition can be prepared by mixing the polymeric components or by the forming a block or graft copolymer containing the polymeric components. A mixture of the components can be prepared using, for example, a two-roll mill, an internal mixer, such as a Brabender or Banbury mixer, an extruder, e.g., twin-screw extruder, or the like. Block and graft copolymers can be prepared by appropriate methods depending on the particular nature of the components used. Typical preparatory methods can be found, for example, in the "Block and Graft Copolymerization", R. J. Ceresa (Zd), 1973, Vol. 1 & 2, Wiley-Interscience, New York and "Block Copolymers", D. C. Allport and W. H. Jane, 1973, Wiley, New York.

Generally, the ratio of non-hydrophilic polymeric component to hydrophilic polymeric component is 0.65:1 to 9:1. Preferably the ratio of the polymeric components is 1:1 to 9:1.

The polymeric components are selected to provide a multiple phase system. Generally, the polymeric components each have a molecular weight of at least about 3,000 preferably at least about 5,000 and most preferably at least about 10,000.

As stated above, the relative amounts of non-hydrophilic and hydrophilic polymeric components are selected, depending on the particular materials employed, to provide the desired properties. Due to the presence of the hydrophilic polymeric component, the composition is capable of being hydrated by the absorption of water. As water is absorbedby the composition, it may soften with a softening ratio of at least about 2:1, preferably at least 6:1, more preferably at least about 10:1, most preferably at least about 20:1, and in particular about 40:1. The term "softening ratio " is used here into refer to the ratio of the 2.5% Secant modulus values of the composition in the form of a tubular article, when substantially non-hydrated, to the 2.5% Secant modulus of the composition when substantially completely hydrated. The term "substantially completely hydrated " refers to the state of the composition when it is in equilibrium with an excess of water at 37° C. and ambient pressure.

The composition may swell on absorption of water with a swelling ratio of at least about 1.3:1, preferably at least about 1.7:1 and most preferably at least about 2.0:1. The term "swelling ratio " refers to the ratio of the volume of a given sample of the composition when substantially completely hydrated to its volume of a given sample of the composition when substantially completely non-hydrated.

Preferably the composition both softens and swells when placed in the body.

When substantially completely hydrated the composition has a tensile energy to break of at least about 700 Newton-centimeters per cubic centimeter (N-cm/cm$^3$), preferably at least about 1,400 N-cm/cm$^3$ and most preferably about 1,700 N-cm/cm$^3$. The term "tensile energy to break " (TEB) is defined in ASTM-D882 as the area under the stress-strain curve or $$TEB = \int_0^{\epsilon_T} S d\epsilon$$

where S is the stress at any strain, $\epsilon_i$; and $E_T$ is the strain at rupture. The tensile energy to break provides an indication of the toughness of the hydrated composition and its ability to withstand the conditions it will be subjected to in use.

It will be readily appreciated that when a tubular product such as a cannula is withdrawn from the body it is extremely important that it does not tear or break leaving pieces remaining inside the body. Neither tensile strength nor elongation to break are good indicators of toughness. Brittle materials and notch sensitive materials can have tensile strengths. Extremely weak materials can have elongation but not the strength to survive extraction. TEB is a measure of the energy required to break and is a combination of these two important criteria.

The ultimate elongation of the multiple phase composition should be at least about 10%, preferably at least about 25% and most preferably at least about 50%.

The composition when substantially completely hydrated has a 2.5% Secant modulus of less than about 7,000 Newtons/square centimeter ($N/cm^2$), preferably less than about 3,500 $N/cm^2$ and most preferably less than about 2,000 $N/cm^2$. When substantially completely hydrated the 2.5% Secant modulus can be as low as about 30 $N/cm^2$ preferably above about 60 $N/cm^2$ and most preferably above about 120 $N/cm^2$.

Typically the 2.5% Secant modulus of the composition when substantially non-hydrated is at least about 15,000 $N/cm^2$ when used as an over the needle catheter. Preferably the 2.5% Secant modulus of the composition is at least about 28,000 $N/cm^2$. Preferably the 2.5% Secant modules of the cannula 10 reduces more than about 3:1, more preferably more than about 10:1 and still more preferably at least about 20:1 upon formation of the enlarged duct cross-section 24.

The composition may be crosslinked if desired. Cross linking of the composition gives the polymeric composition strength above the melting or softening points of the polymeric components permitting sterilization of a device utilizing the composition at above that temperature. This is particularly advantageous if the polymeric component of the continuous phase has a relatively low melting or softening point. Crosslinking of the composition may also be used to adjust the 2.5% Secant modulus of the composition to bring it to the desire value for the proposed use of the composition. When the composition comprises a physical mixture of the non-hydrophilic and hydrophilic components, crosslinking of the mixture can control the tendency of the hydrophilic component to leachout of the composition when it is in extended contact with water or body fluids. Cross linking may also improve the toughness (TEB) of the composition in the hydrated state.

Cross linking of the composition can be effected by use of an appropriate crosslinking agent or by irradiation, preferably in the presence of a crosslinking promoter, such as triallyl isocyanurate, or the like. In a preferred embodiment the composition is crosslinked by high energy radiation from an electron accelerator. The amount of irradiation should be in the range of about 0.5 to about 30 Megarads (Mrads) preferably about 0.5 to about 15 Mrads and most preferably about 0.5 to about 10 Mrads.

Either or both components of the composition may contain additional ingredients such as stabilizers, antioxidants, radioopacifiers, medicaments, fillers or the like. For certain applications it may be advantageous to incorporate a water soluble or water dispersible medicament which can leach from the composition of the cannula when it contacts body fluids. Such medicaments include anti-thrombogenic agents, antibiotics, anti-viral agents, anticoagulants, anti-inflammatory agents or the like.

The cannula should not swell or soften appreciably during the time it is being inserted in a vein or the like. It has been found that the time for the cannula to swell to 50% of its fully swollen volume should be at least about 15 seconds, preferably at least about 60 seconds.

An alternative material which may be utilized as a cannula material such that an inner cross-section of the duct increases to form an enlarged duct cross-section is a thermoplastic material with temperature sensitive (softens with temperature) and/or shape-memory properties. Such polymeric compounds are described, for example, in the following articles: "Softenable, Shape-Memory Thermoplastics for Biomedical Use", R. S. Ward, K. A. White, J. S. Riffle, Second World Congress on Biomaterials, 10th Annual Meeting of the Society for Biomaterials, Washington, D.C., Apr. 27–May 1, 1984. The aforementioned thermoplastic materials comprise a base polymer that is a block or segmented copolymer thermoplastic with at least one block type which has an abrupt glass transition temperature ($T_g$) at or greater than room temperature, but less than approximately body temperature. The remainder of the base polymer contains hard blocks whose dominant thermal transition is substantially greater than body temperature. The cannulae are originally made with their eventually desired expanded internal diameter and then are heated above the glass transition ($T_g$), drawn out to form longer and thinner cannulae and held in this state until cooled below the($T_g$). Once the longer and thinner cannulae have warmed to a temperature that is greater than room temperature, i.e., once the cannulae have reached the glass transition temperature, $T_g$, the shape-memory properties operate and the cannulae increase in internal and external diameter while shrinking in length and while also softening.

In accordance with an embodiment of the present invention the cannula 10 can be made of a material through which medicaments can diffuse and therein forcing tube 36 can be made of a material which is substantially impervious to medicaments. In this manner medicaments can be delivered through the cannula 10 without irritating the skin 26 in those instances when the reinforcing tube 36 extends beneath the skin 26 and prevents the medicants from exiting the cannula 10 at skin level. By the term "medicaments" is meant organic chemical compounds (pharmaceuticals) which have sufficient solubility to be taken up in the body.

Industrial Applicability

In accordance with the present invention a cannula 10 is set forth which is useful for the introduction of medicaments and nutrients to and/or extraction of body fluids from a patient. A portion of the cannula 10 which extends externally at the skin of the patient is protected from kinking.

While the invention has been described in connection with specific embodiments thereof, it will be understood that it is capable of further modification, and this application is intended to cover any variations, uses, or adaptions of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. In a cannula having a proximal end portion adapted to be connected to a hub, a distal end portion and a longitudinal duct therethrough from the distal end portion to the proximal end portion, the cannula being of a material selected such that an inner cross-section of the duct increases to form an enlarged duct cross-section when at least a part of the distal end portion is inserted through the skin and into a blood vessel of a living subject and maintained therein and/or when the duct is contacted by an aqueous liquid for a period of time sufficient for the enlarged duct cross-section to form, an improvement comprising:

where in the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position.

2. A cannula as set forth in claim 1, wherein the inner passageway has an inside cross-section substantially equal to or greater than the enlarged duct cross-section at the distal end portion.

3. A cannula as set forth in claim 1, wherein the reinforcing tube is of a polymeric material.

4. A cannula as set forth in claim 1, wherein the reinforcing tube is of a plastic material.

5. A cannula as set forth in claim 1, wherein the cannula is of a material having a 2.5% Secant modulus which reduces more than about 3:1 upon formation of the enlarged duct cross-section.

6. A cannula as set forth in claim 1, wherein the cannula is of a material through which medicaments can diffuse and wherein the reinforcing tube is of a material substantially impervious to medicaments.

7. A cannula as set forth in claim 1, wherein the cannula includes a tapered section extending from said position towards said proximal end portion to an end of taper location adjacent said position and wherein the reinforcing tube terminates at the end of taper location.

8. A cannula as set forth in claim 7, wherein the tapered section is tapered at an angle of less than about 45°.

9. A cannula as set forth in claim 7, wherein said reinforcing tube is of a polymeric material.

10. A cannula as set forth in claim 7, wherein said reinforcing tube is of a plastic material.

11. A cannula as set forth in claim 7, wherein said cannula is of a material through which medicaments can diffuse and wherein said reinforcing tube is of a material substantially impervious to medicaments.

12. A cannula as set forth in claim 7, wherein the tapered section is tapered at an angle of less than about 15°.

13. A cannula as set forth in claim 7, wherein the tapered section is tapered at an angle of less than about 5°.

14. A cannula as set forth in claim 1, wherein the cannula is an over-the-needle type cannula.

15. A cannula as set forth in claim 1, wherein the inner passageway has an inside cross-section substantially equal to said enlarged duct cross-section.

16. In a cannula having a proximal end portion adapted to be connected to a hub, a distal end portion and a longitudinal duct therethrough from the distal end portion to the proximal end portion, the cannula being of a material selected such that an inner cross-section of the duct increases to form an enlarged duct cross-section when at least a part of the distal end portion is inserted through the skin and into a blood vessel of a living subject and maintained therein and/or when the duct is contacted by an aqueous liquid for a period of time sufficient for the enlarged duct cross-section to form, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position; and wherein the cannula includes a tapered section extending from said position towards said proximal end portion to an end of taper location adjacent said position and wherein the 17. In a cannula having a proximal end portion adapted to be connected to a hub, a distal end portion and a longitudinal duct there through from the distal end portion to the proximal end portion, the cannula being of a material selected such that an inner cross-section of the duct increases to form an enlarged duct cross-section when at least a part of the distal end portion is inserted through the skin and in to a blood vessel of a living subject and maintained there in and/or when the duct is contacted by an aqueous liquid for a period of time sufficient for the enlarged duct cross-section to form, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position; and wherein the cannula includes a tapered section extending from said position towards said proximal end portion to an end of taper location adjacent said position and wherein the reinforcing tube terminates at the end of taper location; and wherein said cannula is of a material having a 2.5% Secant modulus which reduces more than about 3:1 upon formation of said enlarged duct cross-section.

18. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel and where in the cannula is of a material which softens on being inserted into a living subject; and further including:

a reinforcing tube having an outer surface matingly held within the duct and having an inner passageway, the tube extending from the proximal end portion to adjacent the position.

19. A cannula as set forth in claim 18, wherein the inner passageway has an inside cross-section substantially equal to or greater than the duct cross-section at the distal end portion.

20. A cannula as set forth in claim 18, wherein the reinforcing tube is of a polymeric material.

21. A cannula as set forth in claim 18, wherein the reinforcing tube is of a plastic material.

22. A cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position; and wherein the cannula is of a material through which medicaments can diffuse and wherein the reinforcing tube is of a material substantially impervious to medicaments.

23. A cannula as set forth in claim 18, wherein the cannula includes a tapered section extending from said position towards said proximal end portion to an end of taper location adjacent said position and wherein the reinforcing tube terminates at the end of taper location.

24. A cannula as set forth in claim 23, further including:

means for easing the transition from the unreinforced cannula distal of the reinforcing tube to the reinforced cannula proximal the reinforcing tube.

25. A cannula as set forth in claim 24, wherein said means comprises a distal end of said reinforcing tube being thinned to a reduced thickness.

26. A cannula as set forth in claim 23, wherein the tapered section is tapered at an angle of less than about 45°.

27. A cannula as set forth in claim 26, wherein said angle is less than about 15°.

28. A cannula as set forth in claim 27, wherein said angle is less than about 5°.

29. A cannula as set forth in claim 23, wherein the tapered section is tapered at an angle at less than about 15°.

30. A cannula as set forth in claim 23, wherein the tapered section is tapered at an angle of less than about 5°.

31. In a cannula having a proximal end portion adapted to be connected to a hub, a distal end portion and a longitudinal duct therethrough from the distal end portion to the proximal end portion, and improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position, said reinforcing tube having a 2.5% Secant modulus between about 3450 and about 48,000 N/cm$^2$.

32. A cannula as set forth in claim 18, wherein the cannula is an over-the-needle type cannula.

33. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position; and wherein the inner passageway has an inside cross-section substantially equal to said enlarged duct cross-section.

34. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position;

wherein the cannula includes a tapered section extending from said position towards said proximal end portion to an end of taper location adjacent said position and where in the reinforcing tube terminates at the end of tapered location; and means for easing the transition from the unreinforced cannula distal of the reinforcing tube to the reinforced cannula proximal the reinforcing tube, wherein said means comprises a cut away portion in said reinforcing tube beginning and extending proximally from where said reinforcing tube terminates.

35. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located such that when the distal end portion is inserted in the blood vessel the position is located beneath the skin short of the blood vessel; and further including:

a reinforcing tube having an outer surface matingly held within the duct and having an inner passageway, the tube extending from the proximal end portion to adjacent the position;

wherein the cannula includes a tapered section extending from said position toward said proximal end portion to an end of taper location adjacent said position and wherein the reinforcing tube terminates at the end of taper location;

means for easing the transition from the unreinforced cannula distal of the reinforcing tube to the reinforced cannula proximal the reinforcing tube, said means comprising one or more fingers extending from where said reinforcing tube terminates towards said position.

36. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located distally from the hub, the cannula including a tapered section extending from said position toward said proximal end portion to an end of taper location adjacent said position, said tapered section being tapered at an angle of less than about 15°, the cannula being of a material which softens on being inserted into a living subject; and further including:

a reinforcing tube having an outer surface matingly held within the duct and having an inner passageway, the tube extending from the proximal end portion distally beyond the hub towards the position, said reinforcing tube terminating at said end of taper location; and means for easing the transition from the unreinforced cannula distal of the reinforcing tube to the reinforced cannula proximal of the reinforced tube.

37. A cannula as set forth in claim 36, wherein the inner passageway has an inside cross-section substantially equal to or greater than the duct cross-section at the distal end portion.

38. A cannula as set forth in claim 36, wherein the reinforcing tube is of a polymeric material.

39. A cannula as set forth in claim 36, wherein the reinforcing tube is of a plastic material.

40. In a cannula having a proximal end portion adapted to be connected to a hub, a distal end portion and a longitudinal duct therethrough from the distal end portion to the proximal end portion, and improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located distally from the hub, the cannula including a tapered section extending from said position toward said proximal end portion to an end of taper location adjacent said position, said tapered section being tapered at an angle of less than about 15°;

a reinforcing tube having an outer surface matingly held within the duct and having an inner passageway, the tube extending from the proximal end portion distally beyond the hub towards the position, said reinforcing tube terminating at said end of taper location;

means for easing the transition from the unreinforced cannula distal of the reinforcing tube to the reinforced cannula proximal of the reinforcing tube; and wherein the cannula is of a material through which medicaments can diffuse and wherein the reinforcing tube is of a material substantially impervious to medicaments.

41. A cannula as set forth in claim 36, wherein said means comprises a cut away portion in said reinforcing tube, said cut away portion being cut away along a plane at a skew angle to said reinforcing tube, said cut away portion beginning and extending proximally form where said reinforcing tube terminates.

42. A cannula as set forth in claim 36, wherein said means comprises a distal end of said reinforcing tube being thinned to a reduced thickness.

43. A cannula as set forth in claim 36, wherein said angle is less than about 5°.

44. A cannula as set forth in claim 36, wherein the position is located such that when the distal end portion is inserted in the blood vessel the position is located beneath the skin short of the blood vessel.

45. A cannula as set forth in claim 36, wherein the cannula is an over-the-needle type cannula.

46. In a cannula having a proximal end portion adapted to be connected to a hub, a distal end portion and a longitudinal duct therethrough from the distal end portion to the proximal end portion, an improvement comprising:

wherein the cannula has a larger outer cross-section and the duct has a larger inner cross-section starting from the proximal end portion and continuing to a position along the cannula than have the cannula and the duct starting at the distal end portion and continuing to the position, the position being located distally from the hub; and further including:

a reinforcing tube having an outer surface matingly held within the duct and having an inner passageway, the tube extending from the proximal end portion distally beyond the hub towards the position; and means for easing the transition from the unreinforced cannula distal of the reinforced tube to the reinforced cannula proximal of the reinforced tube, said means comprising one or more fingers extending from where said reinforcing tube terminates towards said position.

* * * * *